US007416902B2

(12) United States Patent
Pletcher et al.

(10) Patent No.: US 7,416,902 B2
(45) Date of Patent: Aug. 26, 2008

(54) METHOD AND APPARATUS FOR AIRBORNE PARTICLE SORTING

(75) Inventors: Timothy Allen Pletcher, Eastampton, NJ (US); Peter James Coyle, Newtown, PA (US); Joseph Thomas McGinn, Flemington, NJ (US); David Keller, Newtown, PA (US)

(73) Assignee: Sarnoff Corporation, Princeton, NJ (US)

( * ) Notice: Subject to any disclaimer, the term of this patent is extended or adjusted under 35 U.S.C. 154(b) by 852 days.

(21) Appl. No.: 10/945,251

(22) Filed: Sep. 20, 2004

(65) Prior Publication Data

US 2005/0105079 A1 May 19, 2005

Related U.S. Application Data

(60) Provisional application No. 60/504,682, filed on Sep. 19, 2003.

(51) Int. Cl.
*G01N 1/00* (2006.01)

(52) U.S. Cl. ......................... 436/174; 436/52; 436/153; 436/172; 436/177; 436/181; 422/50; 422/83; 422/82.01; 422/82.05; 422/82.08; 73/23.2; 73/28.01; 73/31.07; 73/37.5; 73/863.21; 204/459

(58) Field of Classification Search ............. 209/127.1, 209/127.4, 131; 96/1, 15, 372, 413, 417; 436/181, 174; 356/72
See application file for complete search history.

(56) References Cited

U.S. PATENT DOCUMENTS

| | | | | |
|---|---|---|---|---|
| 3,853,750 | A * | 12/1974 | Volsy | 209/127.1 |
| 4,318,481 | A * | 3/1982 | Lombardo et al. | 209/3.1 |
| 4,318,482 | A * | 3/1982 | Barry et al. | 209/3.1 |
| 4,318,483 | A * | 3/1982 | Lombardo et al. | 209/3.1 |
| 4,325,483 | A * | 4/1982 | Lombardo et al. | 209/3.1 |
| 5,643,796 | A * | 7/1997 | Van den Engh et al. | 436/50 |
| 6,674,528 | B2 * | 1/2004 | Adachi et al. | 356/336 |
| 6,807,874 | B2 * | 10/2004 | Totoki | 73/864.71 |
| 6,822,180 | B2 * | 11/2004 | Fujii et al. | 209/128 |
| 6,881,246 | B2 * | 4/2005 | Totoki | 96/26 |
| 2002/0053532 | A1 * | 5/2002 | Quake et al. | 209/2 |

* cited by examiner

*Primary Examiner*—Duane Smith
*Assistant Examiner*—Sonji Turner
(74) *Attorney, Agent, or Firm*—Lowenstein Sandler PC

(57) ABSTRACT

An apparatus for airborne particle sorting is provided comprising a charging system adapted for applying an electrostatic charge to the particles, such that particles of at least a first group are deflected to a greater extent than particles of a second group are deflected. A focusing system is adapted for electrostatically focusing substantially at least the particles of the first group into a focused stream that is narrower than the input air stream. A deposition system is adapted for substantially depositing the particles of the first group from the focused stream upon a target surface, where the target surface may be transported to an analysis system capable of analyzing the particles deposited thereon.

24 Claims, 4 Drawing Sheets

METHOD AND APPARATUS FOR AIRBORNE PARTICLE SORTING

CROSS REFERENCE TO RELATED APPLICATIONS

This application claims the priority of U.S. Provisional Patent Application No. 60/504,682, filed Sep. 19, 2003 (entitled "Electrostatically Enhanced Particle Sorting and Deposition"), which is herein incorporated by reference.

FIELD OF THE INVENTION

The present invention generally relates to the sampling of air, and more particularly relates to the collection and sorting of aerosol particles from air samples.

BACKGROUND OF THE INVENTION

There is an increasing demand for air sampling systems for military, private or individual use that are capable of sorting particles of interest (e.g., aerosol particles) from an incoming air sample. Sorting of particles enables a more rapid and accurate analysis of the contents of an air sample by reducing the amount of negligible particles in the sample prior to performing analysis techniques (e.g., such as spectrographic discrimination). Particles of interest are typically separated from other particles in an air sample and then focused onto a target or particle collection surface for further analysis.

Current particle sorting systems employ aerodynamic techniques (e.g., nozzles) for manipulating and focusing particles in a sample air stream. While such sorting systems have performed reasonably well in sorting large particles (e.g., larger than approximately 50 μm), they often perform less reliably when required to manipulate smaller particles (e.g., in the range of approximately 0.5 μm to 10 μm). Moreover, such systems demonstrate less than optimal accuracy in focusing the sorted particles onto a designated target or collection surface, due to the difficulties in balancing multiple flow streams and resultant increases in particle velocity as the stream diameter is compressed.

Therefore, there is a need in the art for an improved method and apparatus for airborne particle sorting.

SUMMARY OF THE INVENTION

In one embodiment, an apparatus for airborne particle sorting comprises a charging system adapted for applying an electrostatic charge to the particles, such that particles of at least a first group are deflected to a greater extent than particles of a second group are deflected. A focusing system is adapted for electrostatically focusing substantially at least the particles of the first group into a focused stream that is narrower than the input air stream. A deposition system is adapted for substantially depositing the particles of the first group from the focused stream upon a target surface, where the target surface may be transported to an analysis system capable of analyzing the particles deposited thereon. In further embodiments, an ion wind is generated within the particle sorting system that enables even more precise particle focusing, particularly for small particles.

BRIEF DESCRIPTION OF THE DRAWINGS

So that the manner in which the above recited embodiments of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

Embodiments of the invention generally provide an apparatus for sorting airborne particles and accurately depositing sorted particles upon a target deposition surface. In one embodiment, the apparatus employs electrostatic charging and focusing mechanisms in order to achieve substantially more accurate particle sorting and deposition than existing sorting systems. Moreover, the inventive apparatus achieves more efficient sorting and deposition even for smaller particles. Those skilled in the art will appreciate that the disclosed system may have applications in other fields as well, including airborne particle collection and low-dose pharmaceutical deposition applications (e.g., inhalers).

Figure 1:
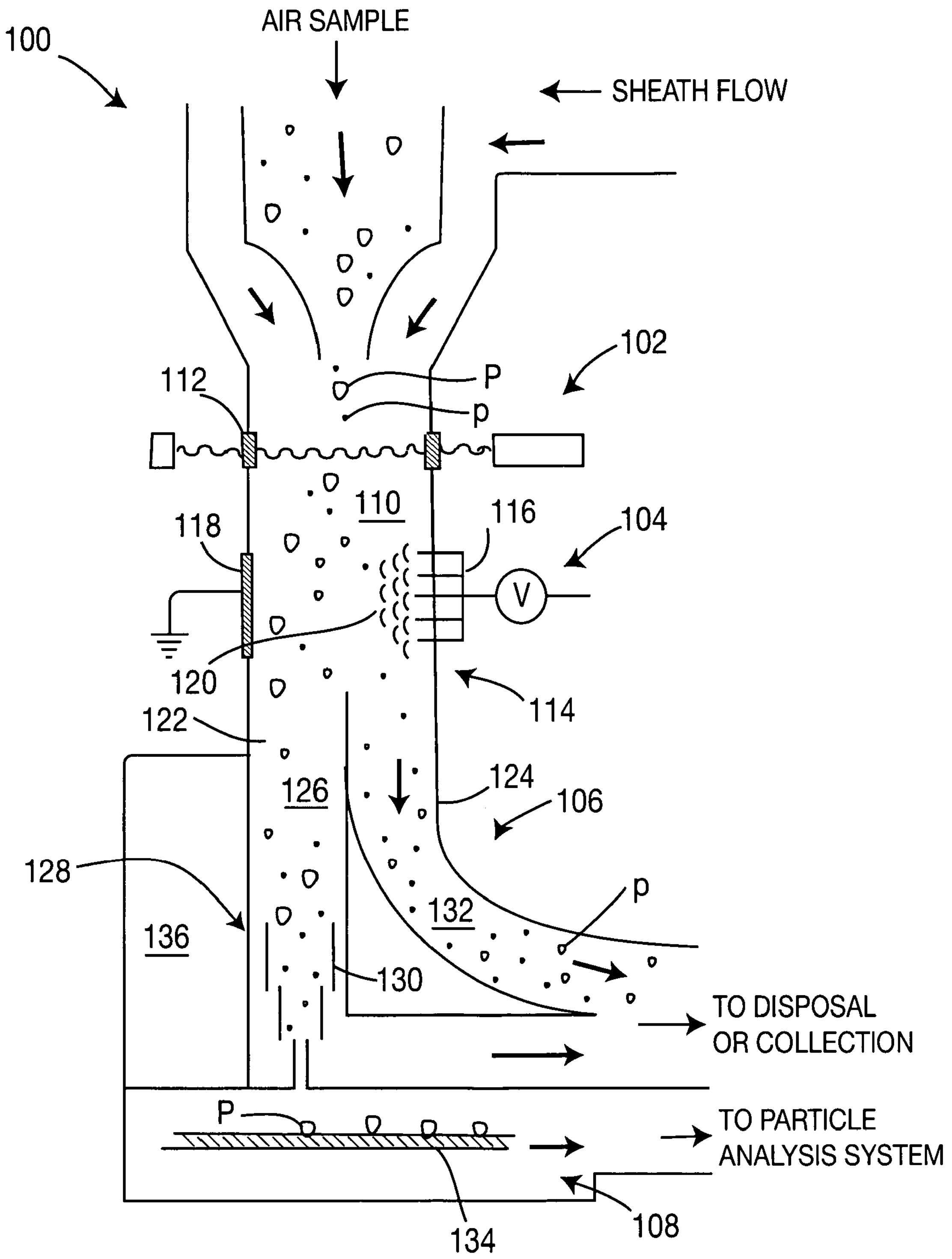
FIG. 1 is a schematic diagram illustrating one embodiment of a particle sorting system according to the present invention.

FIG. 1 is a schematic diagram illustrating one embodiment of a particle sorting system 100 according to the present invention. In one embodiment, the system 100 comprises four main components: a spectrographic identification subsystem 102, a particle charging section 104, a particle focusing section 106 and a particle deposition subsystem 108.

The spectrographic identification subsystem 102 is adapted to receive an incoming air sample (containing one or more different types of particles) and to identify particles of interest within the air sample for further analysis. In one embodiment the spectrographic identification subsystem 102 comprises a flow shaft 110 and an optical detection unit 112 positioned proximate to the periphery of the flow shaft 110. In one embodiment, the optical detection unit 112 is adapted to identify particles based on one or more optically observable properties including, but not limited to, fluorescence, color, particle size, particle shape and the like. In one embodiment, the optical detection unit 112 is adapted to identify particles of interest by sensing scattered light patterns produced by individual particles as they traverse a beam produced by the optical detection unit 112. The optical detection system 112 is further adapted to produce a signal for each particle that indicates the particle's final destination, as discussed in further detail below.

In one embodiment, the spectrographic identification subsystem 102 identifies only a small portion of the particles passing therethrough as being of interest. In one embodiment, the ratio of identified particles to negligible particles is on the order of approximately 1:1,000 to 1:100.

In one embodiment, the spectrographic identification subsystem 102 is adapted to receive the air sample from a virtual impactor or other system within a common sampling device. In addition the spectrographic identification subsystem 102 is adapted to receive a sheath flow. In one embodiment, the sheath flow is a gas (e.g., air or other gas mixture) that is injected into the flow shaft 110 proximate to a location where the flow shaft 110 receives the air sample. The sheath flow is employed to aerodynamically focus particles in the incoming air sample so that the particle trajectories intersect the field of view (e.g., a beam of a laser) of the optical detection unit 112.

In one embodiment, the spectrographic identification subsystem 102 is further adapted to combine the incoming air sample with the sheath flow in the flow shaft 110, in order to form a combined stream for better transporting and focusing particles contained within the air sample to other components of the particle sorting system 100.

In another embodiment, the spectrographic identification subsystem 102 is further adapted to provide a control signal to the particle charging section 104, based on identification of particles of interest (e.g., particles displaying a desired optical property) within the combined stream. The control signal allows the particle charging section 104 to more efficiently charge particles for deposition.

The particle charging section 104 is positioned downstream of the spectrographic identification subsystem 102 and is adapted to charge and deflect particles in the combined stream into appropriate sections of the particle focusing section 106, as described in further detail below. In one embodiment, the particle charging section 104 comprises a radial electrostatic charging mechanism 114 positioned proximate to the periphery of the flow shaft 110. In one embodiment, the electrostatic charging mechanism 114 comprises a plurality of sharpened electrode tips (e.g., mechanically formed at an end of the flow shaft 110). In one embodiment, the electrostatic charging mechanism 114 comprises an array 116 of first electrodes (e.g., corona electrodes) positioned proximate to the periphery of the flow shaft 110 and a second electrode (e.g., a ground electrode or other electrode at a lower voltage than the array 116) 118 positioned across the flow shaft 110 from the array 116, where the array 116 and the ground electrode 118 are adapted to generate an electrostatic field 120 therebetween.

Specifically, the array 116 and the second electrode 118 are adapted to generate an electrostatic field 120 that charges particles in the combined stream. In one embodiment, the electrostatic charging mechanism 114 is adapted to receive a control signal from the spectrographic identification subsystem 102 that enables the electrostatic charging mechanism 114 to efficiently charge particles of interest. In one embodiment, the electrostatic charging mechanism 114 is controlled such that only particles identified by the spectrographic identification subsystem 102 as being of interest are charged. In another embodiment, the electrostatic charging mechanism 114 applies a charge to all particles within the combined stream, and particles of different ratios will therefore acquire different charge-to-radius ratios that dictate their degrees of deflection. The generated electrostatic field is of such strength that particles identified as being of interest (e.g., particles P) are deflected into a first portion of the particle focusing section 106.

In one embodiment, particles flow through the particle charging section 104 in a narrow combined stream and at a velocity of between approximately ten and twenty meters per second, thereby substantially preventing particles from becoming trapped on the second electrode 118. Particles of different sizes are deflected to differing degrees, so that the trajectories of individual particles will vary according to the sizes of the particles, with the largest particles (e.g., largest diameter) being deflected the most. Substantially all particles having the same charge-to-radius ratio will be deflected along a common trajectory. In one embodiment, the electrostatic field 120 completely charges particles that are identified as being of interest, so that charging is uniform for a given particle diameter, thereby ensuring repeatable trajectories for deflected particles.

In one embodiment, the particle charging section 104 is only energized when a particle identified as being of interest by the spectrographic identification subsystem 102 is to be deflected. This reduces the potential electromagnetic radiation interference that may be inflicted upon the optical detection unit 112.

The particle focusing section 106 is positioned downstream of the particle charging section 104 and comprises a first portion 122 and a second portion 124 that branch off from the flow shaft 110 in divergent directions. The first portion 122 of the particle focusing section 106 is adapted to receive particles that have been identified as being of interest by the spectrographic identification subsystem 102 and appropriately charged and deflected by the particle charging section 104. The first portion 122 of the particle focusing section 106 comprises a first sorting shaft 126 having positioned therein an electrostatic focusing mechanism 128 adapted for focusing the stream of deflected particles into a narrower stream for deposition. In one embodiment, the electrostatic focusing mechanism 128 comprises an electrostatic lens 130.

Figure 3:
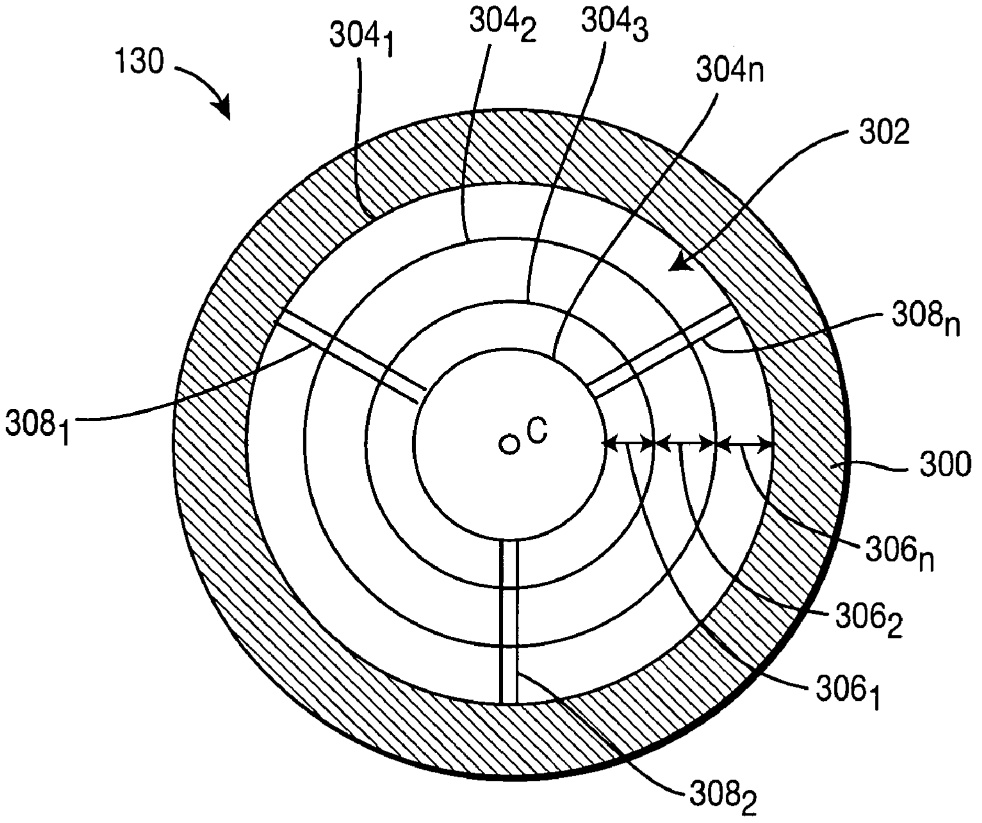
FIG. 3 is a top view illustrating one embodiment of an electrostatic lens for use in the particle sorting system.

FIG. 3 is a top view illustrating one embodiment of an electrostatic lens 130 for use in the particle sorting system 100. In one embodiment, the electrostatic lens 130 comprises a lens housing 300 and a convergence-style lens 302. In one embodiment, the lens housing 300 is a cylindrical housing configured to protect the convergence-style lens 302, which is housed therein. In one embodiment, the lens housing 300 is formed of a dielectric material.

In one embodiment, the convergence-style lens 302 comprises a plurality of thin-walled conductive tubes $\mathbf{304}_1$-$\mathbf{304}_n$ (hereinafter collectively referred to as "tubes 304"). Each of the plurality of conductive tubes 304 has a different diameter, and the conductive tubes 304 are arranged in a concentric fashion so that the further inward a tube 304 is radially, the smaller the diameter of the tube 304 is. In one embodiment, the tubes 304 are precision-aligned within each other and within the lens housing 300, so that each tube 304 is separated from the next by a radial air gap $\mathbf{306}_1$-$\mathbf{306}_n$ (hereinafter collectively referred to as "air gaps 306"), and the tubes 304 share a common central axis C, which is the central axis of the electrostatic lens 130.

The effectiveness of the convergence-style lens 302 is dependent upon a plurality of parameters including the sequential tube diameters, differential voltages between successive tubes 304, individual tube lengths and the sizes of the radial air gaps 306 between neighboring tubes 304. In one embodiment, these parameters may be optimized using electrostatic analysis software.

In one embodiment, the individual focusing sections (e.g., tubes 304) of the electrostatic lens 130 are configured in an alternating polarity mode. In another embodiment, the individual tubes 304 of the electrostatic lens 130 are configured in a sequential step voltage configuration. The sequential step voltage configuration will typically result in a more compact and efficient design; however, depending on the number of tubes 304 used, the peak voltage in the innermost tube 304 may be quite high. This may result in larger particles being moved toward the central axis C of the electrostatic lens 130 more quickly than smaller particles; thus, in one embodiment, the central axis C of the electrostatic lens 130 is positioned to be coincident with the deflection trajectory of the smaller particles. In this manner, the smaller particles will have the shortest distance to traverse to reach the central axis C of the electrostatic lens 130.

In one embodiment, the concentric plurality of tubes 304 is supported by two or more radial fins $\mathbf{308}_1$-$\mathbf{308}_n$ (hereinafter referred to as "fins 308") that extend inward from the outermost tube $\mathbf{304}_1$ to the innermost tube $\mathbf{304}_n$. In one embodiment, the radial fins 308 are constructed as thinly as possible so as not to obstruct flow through the tubes 304, as discussed in further detail below.

In operation, the portion of the combined stream that is diverted into the electrostatic lens 130 flows through each successive air gap 306 of the electrostatic lens 130 as the combined stream flows from the entrance of the lens to the exit (e.g., toward the central axis C). As the combined stream flows through the successive air gaps 306, the combined stream becomes more and more narrowly focused, until it exits the electrostatic lens 130. The flow velocity through the outermost (largest diameter) or entrance tube $\mathbf{304}_1$ is substantially equal to the flow velocity through the innermost (smallest diameter) or exit tube $\mathbf{304}_n$. The volumetric flow rate inside each tube 304 decreases in a radially inward manner. Conversely, the volumetric flow rate outside each tube 304 increases in a radially outward manner as particles proceed from the entrance of the electrostatic lens 130 to the exit, at which point a majority of the combined flow is conducted away from the particle deposition subsystem 108 and toward the second portion 124 of the particle focusing section 106, as described in further detail below.

Referring back to FIG. 1, the second portion 124 of the particle focusing section 106 comprises a second sorting shaft 132 that diverges from the first sorting shaft 126 and is adapted to transport a portion of the combined stream containing mostly negligible particles. In one embodiment, the second sorting shaft 132 transports these negligible particles to a collection system or section for disposal.

The particle deposition subsystem 108 is positioned downstream of the particle focusing section 106, and, more specifically, is positioned downstream of the narrowest portion (e.g. innermost tube $\mathbf{304}_n$) of the electrostatic focusing mechanism 128 (e.g. innermost tube $\mathbf{304}_n$ of electrostatic lens 130). The particle deposition subsystem 108 comprises a target surface 134 upon which sorted and focused particles of interest (e.g., particles P) are deposited for further analysis (e.g., by a Raman detection system 136 or other spectrographic interrogation system). In one embodiment, the target surface 134 is a translating surface such as a tape that transports deposited particles to a particle analysis system (not shown). In one embodiment, the portion of the target surface 134 upon which particles are deposited has a diameter of 500 micron or less.

In one embodiment of operation, an air sample (e.g., an aerosol flow) is received by the particle sorting system 100, and more specifically is received by the spectrographic identification subsystem 102. At the same time, a sheath flow is also received by the particle sorting system 100, and this sheath flow combines with the air sample to form a combined flow that is carried past the optical detection unit 112. The optical detection unit 112 identifies particles of interest within the combined flow (e.g., by producing control signals for each particle that indicates the particle's final destination), based on one or more optically observable properties as discussed above. In one embodiment, the spectrographic identification subsystem 102 provides a control signal to the particle charging section 104 based on the optical detection unit's observation of particles of interest.

As the combined flow is carried past the particle charging section 104, the array of first electrodes 116 generates an electrostatic field 120 in conjunction with the second electrode 118 that charges the particles contained within the combined flow. The particles are charged such that the particles identified as being of interest are deflected from a center of the combined flow (e.g., toward the first sorting shaft 126 of the particle focusing section 106). In one embodiment, the signals produced by the optical detection unit 112 are output to the particle charging section 104, which modulates the electrostatic field 120 in an appropriate manner to facilitate particle deflection. In one embodiment, the electrostatic field 120 is modulated by a high-speed switching circuit.

Negligible particles (e.g., particles p) are deflected to a lesser degree than the particles that are of interest, and thus a first portion of the combined stream containing mostly negligible particles is carried to the second sorting shaft 132, which ultimately delivers the first portion of the combined stream to a collection device or other apparatus for disposal.

A second portion of the combined stream containing deflected particles (i.e., particles of interest) is carried to the first sorting shaft 126. The second portion of the combined stream then passes through the electrostatic lens 130, where the deflected particles are focused in a progressively more narrow fashion. After being focused through the narrowest portion (e.g., tube $\mathbf{304}_n$) of the electrostatic lens 130, the deflected particles are delivered to the particle deposition subsystem 108, where the deflected particles are deposited upon the target surface 134. The target surface 134, including the deposited particles, is then delivered to a particle analysis system for analysis of the particles deposited thereon.

The particle sorting system 100 achieves substantially more accurate particle deposition than existing sorting systems, and moreover achieves more efficient sorting and deposition even for smaller particles. This is attributable in part to the use of electrostatic mechanisms (e.g., electrostatic lens 130) for focusing the particles, which achieves a low velocity, tightly focused particle stream that facilitates deposition on the target surface 134. Thus, greater control over the deposition location of the focused particles is achieved than with conventional aerodynamic techniques.

Figure 2:
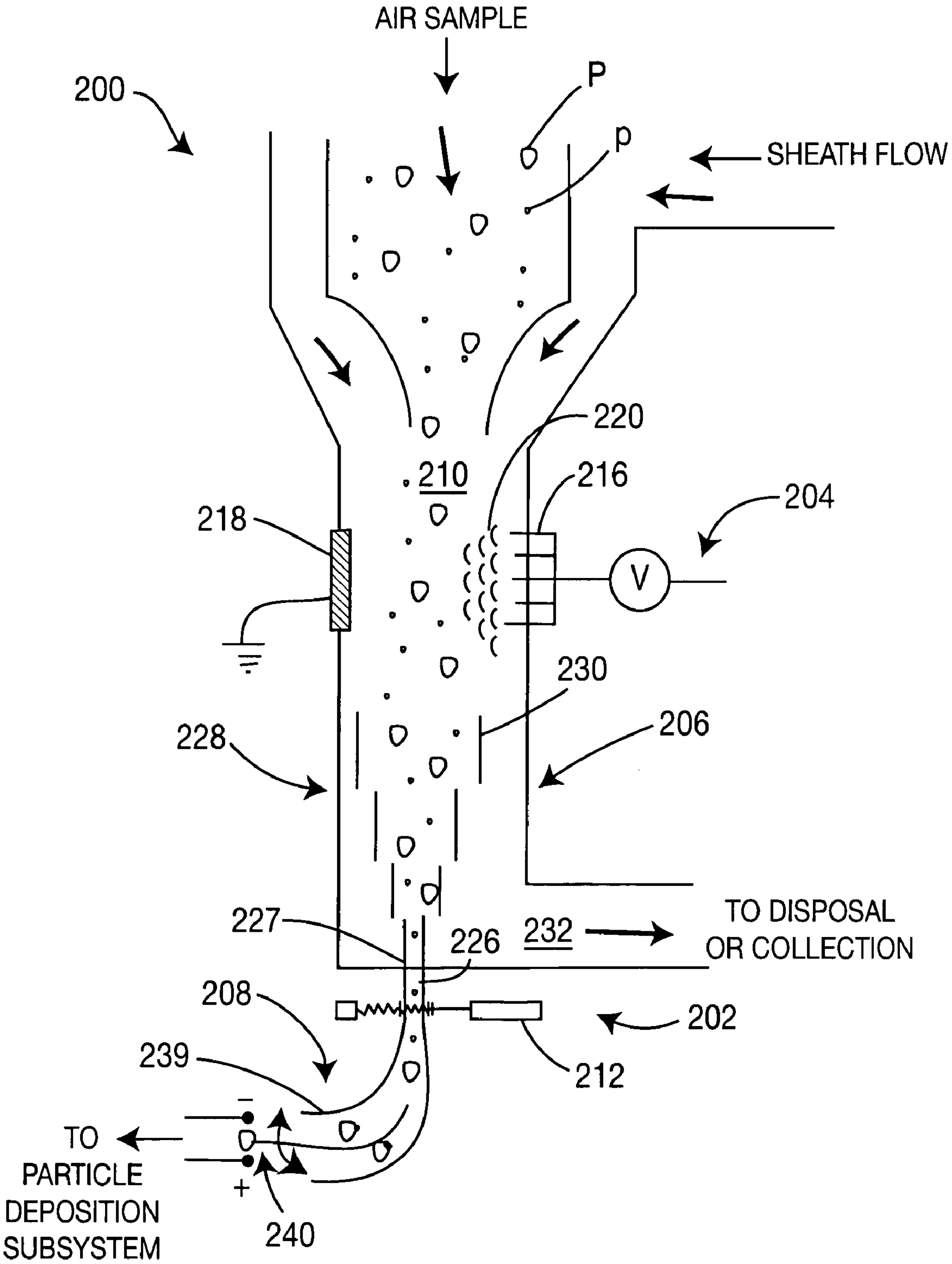
FIG. 2 is a schematic diagram illustrating a second embodiment of a particle sorting system according to the present invention.

FIG. 2 is a schematic diagram illustrating a second embodiment of a particle sorting system 200 according to the present invention. In one embodiment, the system 200 is substantially similar to the particle sorting system 100 illustrated in FIG. 1 and comprises four main components: a spectrographic identification subsystem 202, a particle charging section 204, a particle focusing section 206 and a particle deposition subsystem 208. However, the four main components of the system 200 are configured in a slightly different manner with respect to the configuration of the particle sorting system 100.

In one embodiment, the particle charging section 204 comprises a flow shaft 210 that is adapted to receive an incoming air sample (containing one or more different types of particles). In addition the flow shaft 210 is adapted to receive a sheath flow that combines with the incoming air sample to form a combined stream for better transporting particles contained within the air sample to other components of the particle sorting system 200. Like the particle charging section 104, the particle charging section 204 comprises an array 216 of first electrodes and a second electrode 218 that generate an electrostatic field 220 within the combined flow to charge the particles contained therein.

The particle focusing section 206 is positioned downstream of the particle charging section 204 and comprises the flow shaft 210 and a disposal shaft 232 that branches off from the flow shaft 210 in a divergent direction. The portion of the flow shaft 210 located within the particle focusing section 206 further comprises an electrostatic focusing mechanism 228 positioned therein and adapted for focusing the stream of charged particles into a narrower stream for deposition. In one embodiment, the electrostatic focusing mechanism 228 comprises a convergence-style electrostatic lens 230 similar to the electrostatic lens 130 illustrated in FIG. 3. The disposal shaft 232 diverges from the flow shaft 210 and is adapted to transport an unfocused portion of the combined stream away from the particle sorting system 200.

The spectrographic identification subsystem 202 is positioned downstream of the particle focusing section 206 and is adapted to identify particles of interest within the focused combined stream. In one embodiment the spectrographic identification subsystem 202 comprises an optical detection unit 212 and a focused flow shaft 226. The optical detection unit 212 is positioned proximate to the narrowest portion of the electrostatic focusing mechanism 228, at a first end 227 of the focused flow shaft 226. In one embodiment, the optical detection unit 212 is adapted to identify particles based on one or more optically observable properties including, but not limited to, fluorescence, color, particle size and the like. In one embodiment, the spectrographic identification subsystem 202 is adapted to provide a control signal to a polarity switched target surface, as described in further detail below, in order to deposit particles of interest in a more efficient manner.

The particle deposition subsystem 208 comprises the focused flow shaft 226, a polarity switch 240 and a target surface (e.g., 400 of FIG. 4) upon which selected particles are collected for further analysis. The polarity switch 240 is positioned at a remote end 239 of the focused flow shaft 226, downstream of the optical detection unit 212. The target surface is likewise positioned at the remote end 239 of the focused flow shaft 226, proximate to the polarity switch 240.

The polarity switch 240 is adapted to switch the polarity of the target surface such that particles identified by the spectrographic identification subsystem 202 as being of interest are drawn to and collected upon the target surface, and negligible particles are either deflected away or collected upon an alternate surface. The target surface may be configured in a manner substantially similar to the target surface 134 of FIG. 1, or alternatively may have a different configuration.

Figure 4:
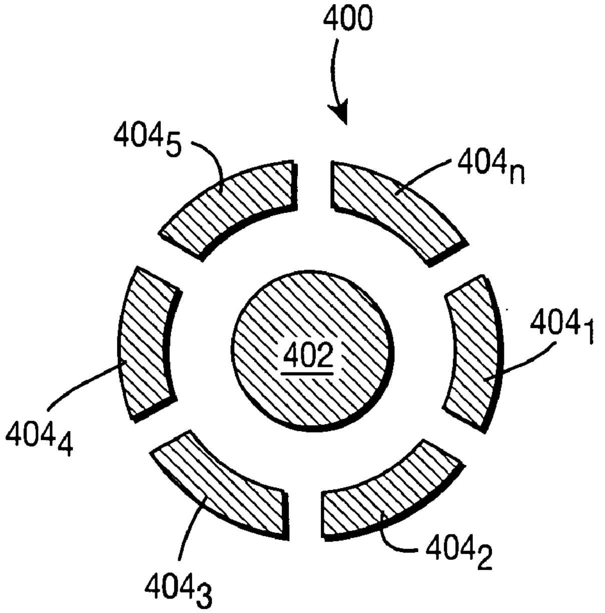
FIG. 4 is a top view of one embodiment of a target surface for use in the particle sorting system illustrated in FIG. 2.

FIG. 4 is a top view of one embodiment of a target surface 400 for use in the particle sorting system 200 illustrated in FIG. 2. In one embodiment, the target surface 400 comprises a first electrode 402 and at least one second electrode $404_1$-$404_n$ (hereinafter referred to as "second electrodes 404"). In one embodiment, the first electrode 402 has a substantially circular cross section, and the second electrode 404 has a substantially ring-shaped cross section that is positioned concentrically around the first electrode 402. In one embodiment, the second electrode 404 is a single ring shaped electrode. In another embodiment, the second electrode 404 comprises a plurality of electrodes 404, each of which forms a segment of ring.

By modifying the polarity of an electric field between the first and second electrodes 402 and 404, charged particles can be drawn selectively onto either the first electrode 402 or one or more of the second electrode(s) 404 for collection. For example, the polarity of the target surface 400 may be set such that particles of interest deposit upon the first electrode 402, and negligible particles deposit upon the second electrodes 404, or vice versa. In one embodiment, particles of deposit directly onto the surfaces of the electrodes 402 or 404. In another embodiment, the surfaces of the electrodes 402 and 404 are covered with a removable semiconductive material through which the electric field extends (e.g., above the surfaces of the electrodes), and particles deposit upon this removable material. Those skilled in the art will appreciate that although the target surface 400 has been illustrated as comprising electrodes 402 and 404 with substantially round or ring-shaped cross sections, any configuration, shape and number of electrodes may be used.

In one embodiment of operation, an air sample (e.g., an aerosol flow) is received by the particle sorting system 200, and more specifically is received by the particle charging system 204. At the same time, a sheath flow is also received by the particle sorting system 200, and this sheath flow combines with the air sample to form a combined flow that is carried past the electrostatic field 220 generated between the array 216 of corona electrodes and the ground electrode 218. The particles are charged by ions formed at the array 216 of corona electrodes and are forced toward the focusing mechanism 228 by the electric field formed between the array 216 of corona electrodes and the focusing electrodes.

The combined stream including the charged particles then passes through the electrostatic lens 230, which focuses the particles into a narrow, low-velocity stream. After being focused through the narrowest portion (e.g., tube $\mathbf{304}_n$) of the electrostatic lens 230, the particles are delivered to the optical detection unit 212 of the spectrographic identification subsystem 202. The optical detection 212 unit identifies particles of interest within the combined flow, based on one or more optically observable properties as discussed above.

The polarity switch 240 switches the polarity of the target surface such that particles identified by the optical detection unit 212 as being of interest (e.g., particles P) are drawn toward and deposit upon the target surface, such as first electrode 402, and negligible particles (e.g., particles p) are deposited onto the surface of at least one of the second electrodes 404. The target surface, including the deposited particles, is then delivered to a particle analysis system for analysis of the particles deposited thereon.

In an alternative embodiment, the particle charging section 204 may be positioned downstream of the spectrographic identification subsystem 202, rather than upstream, so that particles are charged only after being focused and identified. In this embodiment, the array 216 of first electrodes that form the particle charging section 204 will generate an electric field with the electrodes 402 and 404 of the target surface, such that an ion wind is created therebetween. The ion wind functions as a mechanical means for further focusing particles within the combined stream, and is especially useful for focusing and controlling the trajectories of small particles.

The particle sorting system 200, like the particle sorting system 100, achieves substantially more accurate particle deposition than existing sorting systems, and moreover may be configured to achieve more efficient sorting and deposition even for smaller particles (e.g., where charging is performed after spectrographic interrogation). Alternatively, the charging of particles prior to spectrographic interrogation greatly reduces the likelihood of electromagnetic radiation from the particle charging section interfering with the operation of the optical detection unit. In some embodiments, the particle sorting system 200 may be constructed in a manner that is more compact than the particle sorting system 100.

Figure 5:
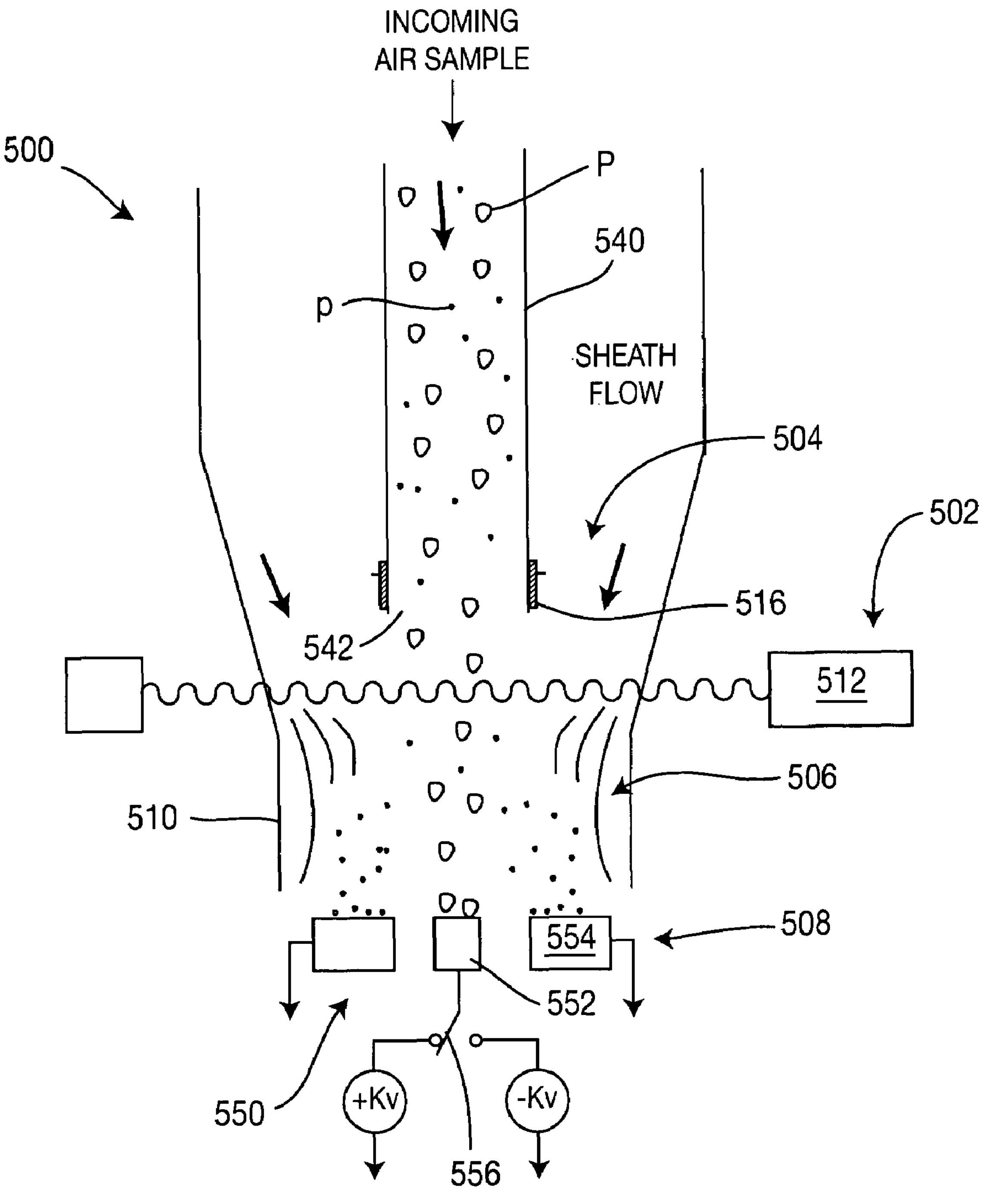
FIG. 5 is a schematic diagram illustrating a third embodiment of a particle sorting system 500 according to the present invention.

FIG. 5 is a schematic diagram illustrating a third embodiment of a particle sorting system 500 according to the present invention. In one embodiment, the particle sorting system 500 comprises four main components: a spectrographic identification subsystem 502, a particle charging section 504, a particle focusing section 506 and a particle deposition subsystem 508. However, these four main components of the system 500 are configured in a manner that is different with respect to the configuration of the components of the particle sorting systems 100 and 200 discussed above.

In one embodiment, the particle charging section 504 comprises an air sample shaft 540 and an array of electrodes 516. The air sample shaft 540 is adapted to deliver an air sample to the particle sorting system 500 (e.g., from a virtual impactor or other sample collection means), and includes a first end 542 that opens into a larger flow shaft 510 or deposition chamber, where the air sample combines with a sheath flow to form a combined flow. The array of electrodes 516 is positioned around the periphery of the air sample shaft 540, proximate to the open first end 542. The array 516 of electrodes is adapted to generate an electric field in the region of the open first end 542 of the air sample shaft 540.

The spectrographic identification subsystem 502 is positioned downstream of the particle charging section 504 and is adapted to identify particles of interest within the combined stream. In one embodiment the spectrographic identification subsystem 502 comprises an optical detection unit 512 positioned near the periphery of the flow shaft 510. In one embodiment, the optical detection unit 512 is adapted to identify particles based on one or more optically observable properties including, but not limited to, fluorescence, color, particle shape, particle size and the like. In one embodiment, the spectrographic identification subsystem 502 further is adapted to send a control signal to the particle deposition subsystem 508.

The particle deposition subsystem 508 is positioned downstream of the spectrographic identification subsystem 502 and comprises a target surface 550 upon which particles in the combined stream deposit. In one embodiment, the target surface 550 comprises at least one first electrode 552, at least one second electrode 554 and a polarity switch 556. The polarity switch 556 is adapted to switch the polarity of the target surface 550 such that particles of interest are selectively deposited on one of the first or second electrodes 552 or 554 (e.g., in accordance with a control signal received from the spectrographic identification subsystem 502). In one embodiment, the electrodes 552 and 554 of the target surface 550 are formed in a manner similar to the target surface 400 illustrated in FIG. 4. Moreover, the first and second electrodes 552 and 554 are adapted to generate a second electric field with the array 516 of electrodes in the particle charging section 504, so that the particle focusing section 506 is established in the region of this second electric field.

In one embodiment of operation, an air sample is received by the particle sorting system 500, and more specifically is received by the air sample shaft 540. As particles within the air sample pass through the open first end 542 of the air sample shaft 540, the particles encounter the particle charging section 504 and are charged by ions formed at the array 516 of electrodes.

As the charged particles exit the air sample shaft 540, the particles combine with the sheath flow to form a combined stream. The combined stream is carried past the spectrographic identification subsystem 502, which identifies particles of interest (e.g., particles P) within the combined stream. In one embodiment, the spectrographic identification subsystem 502 then sends a control signal to the polarity switch 556 that allows the particle deposition subsystem 508 to collect particles of interest more effectively.

As the combined stream is carried past the particle focusing section 506, the array 516 electrodes that form the particle charging section 504 and the first and second electrodes 552 and 554 of the particle deposition subsystem 508 generate the second electric field therebetween. The second electric field generates an ion wind that further focuses particles of interest within the combined stream. In one embodiment, the ion wind is a substantially cone-shaped wind that controls the trajectory of particles within the combined stream and focuses particles of interest onto the intended electrode 552 or 554.

The polarity switch 556 controls which of the first and second electrode 552 or 554 will be adapted to collect particles of interest thereon. In the embodiment illustrated, the polarity switch 556 is set such that the first electrode 552 collects particles of interest thereupon. Negligible particles (e.g., particles p) collect upon the surface of the second electrode 554.

In this embodiment, the generation of the ion wind between the array 516 electrodes that form the particle charging section 504 and the first and second electrodes 552 and 554 of the particle deposition subsystem 508 provides enhanced trajectory control, especially for smaller particles. Thus, the particle collection system 500 is capable of accurately depositing even small particles (e.g., the range of approximately 0.5 μm to 10 μm) onto a precise target surface.

Thus, the present invention represents a significant advancement in the field of airborne particle sorting. An apparatus is provided that employs electrostatic charging and focusing mechanisms in order to achieve substantially more accurate particle deposition than existing sorting systems. Moreover, the inventive apparatus achieves more efficient sorting and deposition even for smaller particles. Those skilled in the art will appreciate that the disclosed system may have applications in other fields as well, including airborne particle collection and low-dose pharmaceutical deposition applications. It should be noted that the present novel methods are described simultaneously using the figures showing the apparatus according to embodiments of the present invention.

While the foregoing is directed to embodiments of the invention, other and further embodiments of the invention may be devised without departing from the basic scope thereof, and the scope thereof is determined by the claims that follow.

What is claimed is:

1. An apparatus for separating, on a particle by particle basis, at least one particle from a plurality of particles contained within an input air stream, the apparatus comprising:

a flow shaft for pneumatically receiving the plurality of particles, the plurality of particles transversing down the shaft, the flow of particles being focused aerodynamically by a sheath flow;

a particle identification system adapted for identifying the at least one particle, the sheath flow being oriented coaxially down the flow shaft such that the plurality of particles intersect a field of view of the particle identification system;

a particle charging system comprising an array of corona electrodes positioned proximate to a trajectory of said input air stream and a second electrode positioned proximate to said array of corona electrodes, the array of corona electrodes and the second electrode being positioned at a lower position relative to the particle identification system, said array of corona electrodes and said second electrode being adapted to generate a corona charge therebetween for selectively applying the corona charge to the at least one particle within said input air stream in a direction substantially one of perpendicular and parallel to the flow shaft, such that the at least one particle is separable from other particles of the plurality of particles; and a particle deposition system adapted for depositing the at least one particle upon a target surface by means of an electrostatic field, the electrostatic field being applied to the at least one particle substantially simultaneously with the corona charge.

2. The apparatus of claim 1, further comprising:

a particle focusing system adapted for electrostatically focusing substantially the plurality of particles into a focused stream that is narrower than the input air stream.

3. The apparatus of claim 1, wherein said particle identification system is adapted to identify said at least one particle prior to said at least one particle being charged by said particle charging section.

4. The apparatus of claim 1, wherein said particle identification system is adapted to produce a control signal.

5. The apparatus of claim 4, wherein said particle charging system is adapted to receive said control signal and to generate said corona charge that applies said corona charge to the at least one particle in response to said control signal and establishes the electrostatic field for deposition of the at least one particle.

6. The apparatus of claim 5, wherein said particle charging system comprises a switching circuit.

7. The apparatus of claim 2, wherein said particle identification system is adapted to identify said at least one particle after said plurality of particles is focused into said focused stream.

8. The apparatus of claim 1, wherein said particle identification system comprises a spectrographic interrogation system.

9. The apparatus of claim 1, wherein said particle identification system is adapted to identify said at least one particle based on at least one optically observable property.

10. The apparatus of claim 9, wherein said at least one optically observable property comprises at least one of the following: fluorescence, color, particle shape and particle size.

11. The apparatus of claim 1, wherein said corona charge is adapted to charge said at least one particle such that a trajectory of the at least one particle is deflected toward the target surface by the electrostatic field.

12. The apparatus of claim 1, wherein said corona charge is adapted to apply a charge that causes said at least one particle to acquire charge-to-radius ratios that is sufficient to deposit said at least one particle.

13. The apparatus of claim 2, wherein said particle focusing system comprises an electrostatic lens.

14. The apparatus of claim 13, wherein said electrostatic lens is a convergence lens.

15. The apparatus of claim 13, wherein said electrostatic lens is configured in an alternating polarity mode.

16. The apparatus of claim 13, wherein said electrostatic lens is configured in a sequential step voltage configuration.

17. The apparatus of claim 1, wherein said target surface comprises a fixed or a translating target surface.

18. The apparatus of claim 1, wherein said target surface comprises: at least the second electrode comprising two sections, the first section upon which said at least one particle is deposited.

19. The apparatus of claim 18, further comprising: a polarity switch adapted to switch a polarity of said target surface such that said at least one particle is deposited upon the second electrode.

20. The apparatus of claim 1, wherein other particles of the plurality of particles are collected on a second section of the second electrode for disposal or additional analysis.

21. A method for separating at least one particle from a plurality of particles contained within an input air stream, the method comprising the steps of:

pneumatically receiving the plurality of particles by a flow shaft, the plurality of particles traveling down the shaft, the flow of particles being focused aerodynamically by a sheath flow;

identifying the at least one particle by a particle identification system, the sheath flow being directed co-axially down the flow shaft such that the plurality of particles intersect a field of view of the particle identification system;

generating a corona charge between an array of corona electrodes positioned proximate to a trajectory of the input air stream and a second electrode positioned proximate to the array of corona electrodes, the array of corona electrodes and the second electrode being positioned at a lower position relative to the particle identification system;

selectively applying the corona charge to the at least one particle within said input air stream in a direction substantially one of perpendicular and parallel to the flow shaft, such that the at least one particle is separable from other particles of the plurality of particles; and depositing by means of an electrostatic field the at least one particle upon a target surface by a particle deposition system, the electrostatic field being applied to the at least one particle substantially simultaneously with the corona charge.

22. The method of claim 21, further comprising: electrostatically focusing substantially the at least one particle into a focused stream that is narrower than the input air stream.

23. The method of claim 21, wherein said particle identifying step comprises identifying said at least one particle prior to said at least one particle being charged by said array of corona electrodes and said second electrode.

24. The method of claim 22, wherein said particle identifying step comprises identifying said at least one particle after said at least one particle is focused into said focused stream.

* * * * *